United States Patent [19]

Suyama et al.

[11] Patent Number: 4,539,613
[45] Date of Patent: Sep. 3, 1985

[54] LOADING APPARATUS FOR A RECORDING MEDIUM

[75] Inventors: Satoshi Suyama, Neyagawa; Kiyotaka Uehira, Hirakata; Kenji Sanpei, Yahata; Kenichi Sakamoto, Osaka; Koichiro Nakagawa, Takarazuka, all of Japan

[73] Assignee: Matsushita Electric Industrial Co., Ltd., Osaka, Japan

[21] Appl. No.: 484,551

[22] Filed: Apr. 13, 1983

[30] Foreign Application Priority Data

Apr. 13, 1982 [JP] Japan .................................. 57-61597

[51] Int. Cl.$^3$ ............................................. G11B 17/04
[52] U.S. Cl. ...................................... 360/99; 360/97; 360/133
[58] Field of Search .................... 360/86, 93, 96.5, 97, 360/99, 133; 206/444

[56] References Cited

U.S. PATENT DOCUMENTS

| 4,205,355 | 5/1980 | Hamanaka et al. | 360/99 |
| 4,368,495 | 1/1983 | Hamanaka et al. | 360/97 |
| 4,417,289 | 11/1983 | Ragle et al. | 360/133 |

Primary Examiner—Stuart N. Hecker
Assistant Examiner—David J. Severin
Attorney, Agent, or Firm—Wenderoth, Lind & Ponack

[57] ABSTRACT

A loading apparatus for a recording medium comprises a holder for holding a recording medium, a guide provided on the holder, a slide plate mounting thereon, and a raised member which supports the guide when the recording medium is not inserted into the holder and which releases the support when a recording medium is fully inserted into the holder. The holder is urged downward so that, when the guide is released from the raised member, the recording medium moves downward to a loading position. A discharging plate having a cam mounted thereon is also provided. When the discharging plate is pushed, the cam pushes up the guide, thereby returning the holder to an unloading position. Thus, each of the loading and unloading operations is completed only by one manual operation.

6 Claims, 10 Drawing Figures

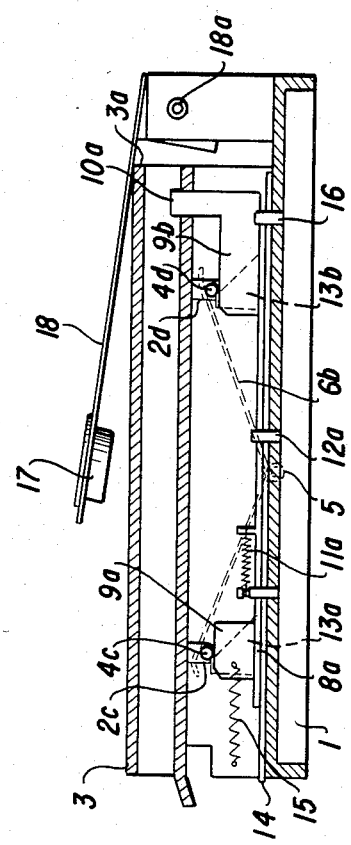

LOADING APPARATUS FOR A RECORDING MEDIUM

BACKGROUND OF THE INVENTION

1. Field of the Invention

This invention relates to a loading apparatus for a recording medium such as a magnetic disk built-in cartridge, which apparatus is used for inserting/discharging the recording medium into/from a magnetic recorder/reproducer, such as a floppy disk apparatus, used in a computer system.

2. Description of the Prior Art

Conventionally, a loading apparatus as shown in FIGS. 1 and 2 is used for a floppy disc apparatus. FIG. 1 is a side sectional view of a main portion of the apparatus, before a cartridge rotatably housing a disk recording medium, such as a magnetic disk, is loaded thereon. FIG. 2 is a side sectional view of the apparatus with the cartridge loaded. Referring to FIGS. 1 and 2 numeral 101 denotes a base body, equipped with a magnetic head (not shown) and various actuators (not shown), on which a holder 103 for holding a cartridge 102 and a cover 106 having a clamp 104 rotatably provided thereon for positioning and holding the cartridge 102 inserted in the holder 103 in a predetermined position on the base 101 are mounted in such a manner as to be urged to turn clockwise around a support pin 109 by means of a compression spring 107 and a tension spring 108, respectively.

To load the cartridge 102 on the loading apparatus as constructed above, the cartridge 102 is inserted into the holder 103 in the direction indicated by arrow A, as shown in FIG. 1. Then the upper end of the cover 106 is manually pushed down and the holder 103 and the cover 106 are turned counterclockwise against the reaction force of the compression and tension springs 107, 108, thereby holding the cartridge 102 between the clamp 104 and the base body 101.

In the loading apparatus having such a construction, the cartridge 102 is inserted and discharged by a turning action, with the support pin 109 as a fulcrum. This results in a disadvantage in that the space required for inserting and discharging the cartridge (as shown in FIG. 1) is large compared with the volume of the apparatus (as shown in FIG. 2) when the cartridge is loaded. Thus, in loading, the area occupied by the apparatus becomes large, which is an obstacle to miniaturization the apparatus. Moreover, the apparatus is not easy to handle, because the operator must not only insert the cartridge 102 into the holder 103 but also turn the holder 103 with respect to the base body 101 to fix it in place. This invention is intended to eliminate the above disadvantage.

SUMMARY OF THE INVENTION

An object of this invention is to provide a loading apparatus for a recording medium which is compact, and occupies small space during loading.

Another object of this invention is to provide a loading apparatus for a recording medium which is constructed by a small number of construction elements compared with conventional loading apparatus so as to be highly reliable.

Still another object of this invention is to provide a loading apparatus for a recording medium which is easy to handle.

The loading apparatus for a recording medium of this invention comprises: a holding means for insertably and dischargeably holding the recording medium, the holding means being reciprocally movable toward and away from a base body and urged in one direction; and a slide plate and a discharging plate which are reciprocally movable perpendicularly to the movement direction of the holding means. Upon loading the recording medium into the holding means, the slide plate is moved in a direction by the recording medium for releasing an engagement between the slide plate and the holding means, whereby the holding means is parallelly moved toward said base body for loading the recording medium together with the holding means at a predetermined position on the base body. Upon discharging the recording medium from the holding medium, the discharging plate is moved by an external force in a direction opposite to the urged direction so that a portion of the discharging plate is brought into abutment on the holding means and moves the holding means away from said base body, whereby the slide plate is automatically returned in the urged direction to engage with the holding means and the recording medium is discharged from the holding means.

BRIEF DESCRIPTION OF THE DRAWINGS

FIGS. 4 through 7A are side section views, showing respective states of the embodiment of the invention shown in FIG. 3.

DESCRIPTION OF THE PREFERRED EMBODIMENTS

Figure 1:
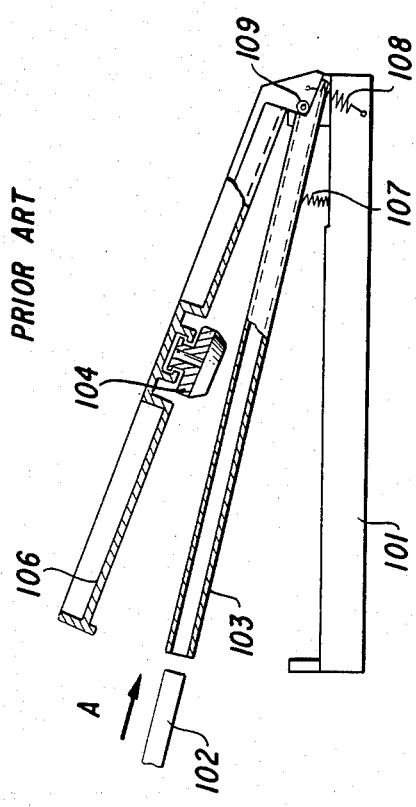
FIG. 1 and FIG. 2 are partially cut away side views showing respective states of the conventional loading apparatus.
Figure 2:
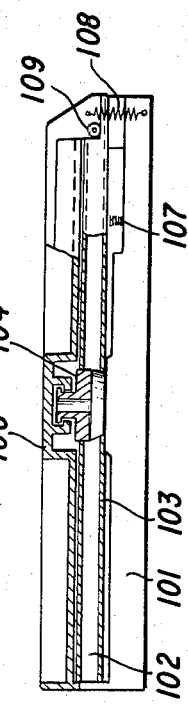
Figure 3:
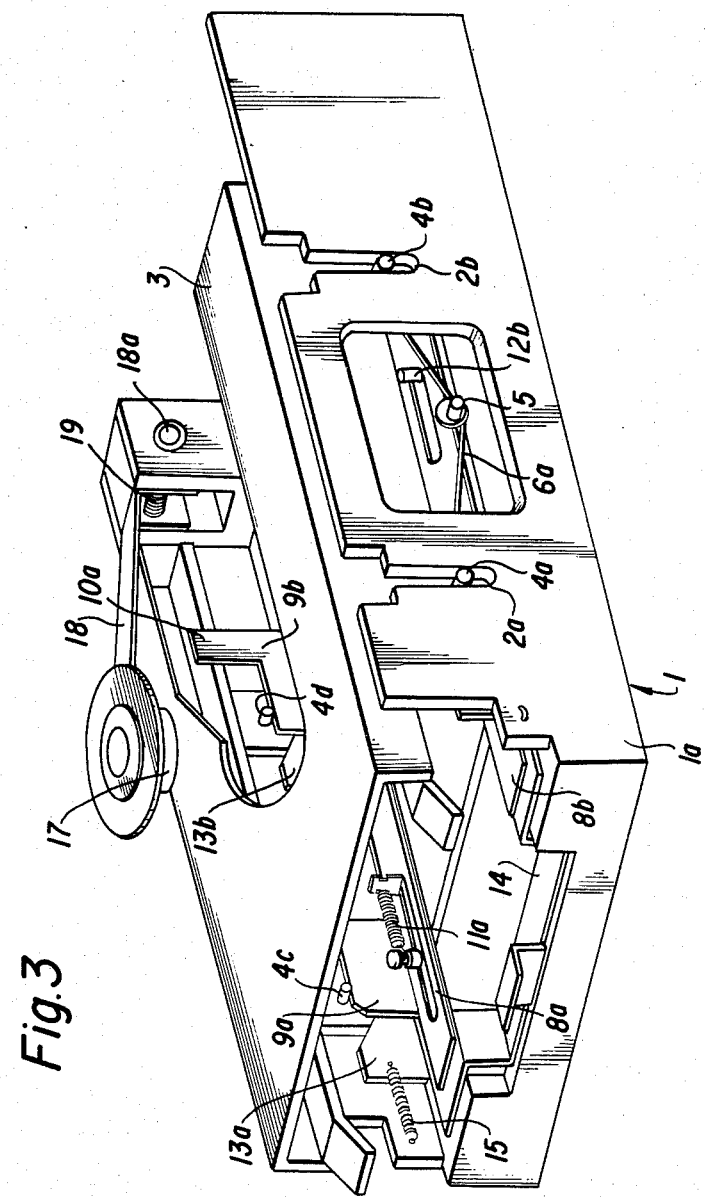
FIG. 3 is an oblique view of an embodiment of a loading apparatus of this invention.

The following is a detailed description of this invention with reference to the drawings. FIG. 3 is an oblique view of an embodiment of this invention, ready to mount a cartridge for recording or reproducing, the cartridge rotatably containing a magnetic disc. FIGS. 4 through 7A the section views of the embodiment at respective states thereof for illustrating its operation. Referring to the figures, numeral 1 denotes a base body into which a magnetic head (not shown) and various actuators (not shown) are to be mounted. The base body 1 is provided with openings, which are long in the vertical direction numbered 2a, 2b on one side wall 1a thereof, and numbered 2c, 2d on the other side wall. Holder guides 4a, 4b, 4c, 4d protrudedly provided on a holder 3 are inserted in the openings 2a, 2b, 2c, 2d so as to be vertically slidable along the openings. The holder 3, supported at its substantial center portion by a pin 5 extendinging from the base body 1, is constantly and movably urged downward by resilient members 6a, 6b composed of torsion spring wires, both ends of the resilient members 6a, 6b being supported by the holder guides 4a, 4b and 4c, 4d. When a cartridge 7 is not inserted in the holder 3, the holder 3, subjected to the pressure of the resilient members 6a, 6b is held at a predetermined position by abutment of the respective ends of the holder guides 4a–4d on raised portions 9a, 9b provided on slide plates 8a, 8b. The above slide plates 8a, 8b are provided at their rear ends with raised portion 10a at a position to abut on the cartridge 7 when the cartridge 7 is inserted into the holder 3. The slide plates 8a, 8b are constantly and movably urged by resilient members 11a in the direction opposite to that of the movement of the cartridge 7 on being inserted, and guided by slide guides 12a, 12b to slide.

A discharge plate 14 for discharging the cartridge 7 is placed at positions overlapping the above slide plates 8a, 8b. This discharge plate 14 comprises cams 13a, 13b which are not in abutment on the holder guides 4a–4d when the cartridge 7 is not loaded, but which, when the cartridge 7 is loaded, move the holder guides 4a–4d along the openings 2a–2d against the resilient force of the resilient members 6a, 6b. The discharge plate 14 is continually urged by a resilient member 15 to move in the direction away from the holder guides 4a–4d, and is guided by a guide shaft 16 to slide.

An arm 18, having a clamp 17 which is rotatably fixed at a leading end of the arm 18 and presses on an upper side of the cartridge 7, is supported at a rear end of the holder 3 by a support shaft 18a so as to be vertically pivotable. The arm 18 is continually urged to pivot toward the base body 1 side by a resilient member 19.

The insertion and discharging operations of the cartridge 7 in this embodiment will be described hereinafter with reference to FIGS. 4 through 7A.

Figure 4:
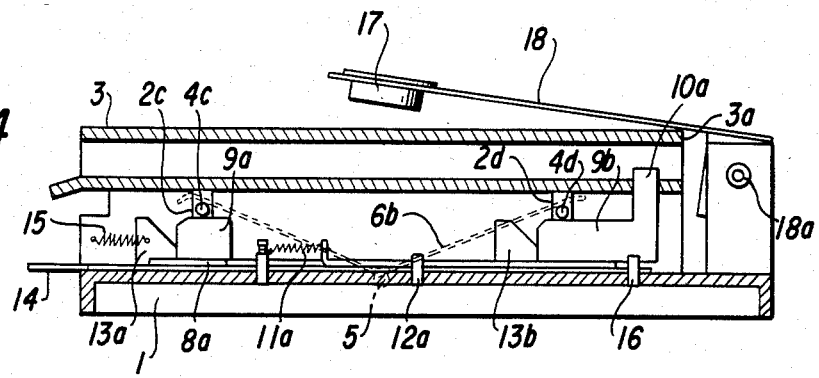

FIG. 4 shows a state in which a cartridge is not loaded. Referring to FIG. 4 in which just a half portion of the loading apparatus is shown, the holder 3 is urged by resilient member 6b downward toward the bottom of the base body 1 and is held at a predetermined position by abutment of the holder guides 4c, 4d resting on the raised portions 9a, 9b of the slide plate 8a. At this position, the clamp 17 is located above the upper surface of the holder 3 by abutment of the arm 18 on the rear end 3a of the holder 3, and does not interfere with the insertion of a cartridge into the holder 3.

Figure 5:
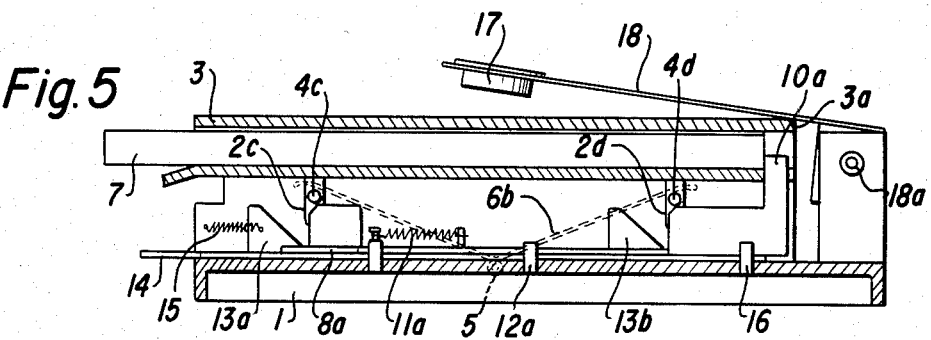
Figure 6:
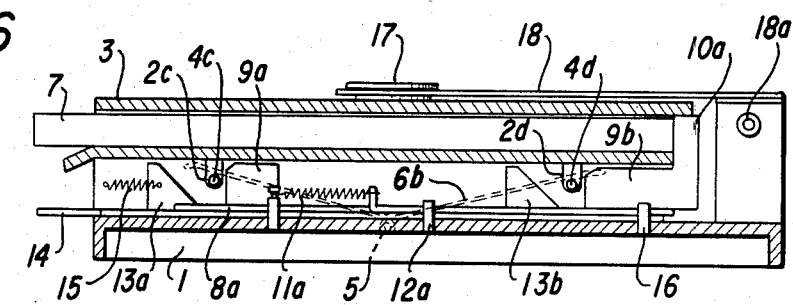

As the cartridge 7 is inserted into the holder 3 next as shown in FIG. 5, the cartridge 7 is brought to abutment on the raised portion 10a at the rear end of the slide plate 8a, causing the slide plate 8a to slide against the tensile force of the resilient member 11a. When the raised portions 9a, 9b of the slide plate 8a are disengaged from the holder guides 4c, 4d thereby to release the restriction, the holder 3, having been movably urged downward by resilient members moves in a vertical direction while keeping its horizontal orientation downward together with the cartridge 7 along the openings 2a–2d, and positions the cartridge 7 in place on the base body 1. With this downward movement of the holder 3, the arm 18 pivots by the resilience of the resilient member 19 (FIG. 3) to press on the upper side of the cartridge 7 as shown in FIG. 6, thus completing the loading.

Figure 7:
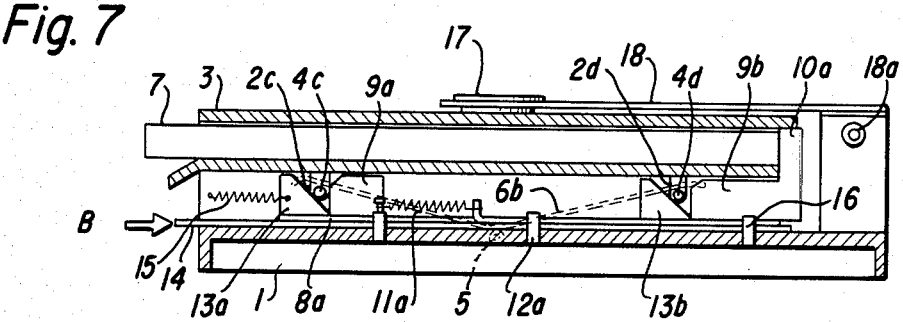

For discharging the cartridge 7, on the other hand, the discharge plate 14 is pushed-in in the direction of arrow B, as shown in FIG. 7, against the tensile force of the resilient member 15, whereby the cams 13a, 13b provided on the discharge plate 14 are brought to abutment on the holder guides 4c, 4d. When the discharge plate 14 is pushed in further, the holder guides 4c, 4d are lifted in a vertical direction while keeping their horizontal orientations along the openings 2a–2d by slopes of the cams 13a, 13b against the resilient force of the resilient members 6a, 6b. When the holder guides 4c, 4d return to the position shown in FIG. 4, the slide plate 8a is inserted by the tensile force of the resilient member 11a beneath the holder guides 4c, 4d, where the raised portions 9a, 9b support the holder 3. At the same time, the arm 18 also rotates clockwise in correspondence with the movement of the holder 3, so that the cartridge 7 discharge is not obstructed, as shown in FIG. 7A.

The loading apparatus of the aforementioned construction allows loading of the cartridge 7 by parallel movement in dimension slightly larger than the thickness dimension of the cartridge. Therefore, unlike the conventional apparatus, the loading apparatus of the invention does not require a large space for loading a cartridge, so that this invention provides a compact loading apparatus. Further, no complicated ring mechanism is necessary so that a loading apparatus having fewer parts and high reliability can be obtained. Operability is also improved because users need only to put the cartridge 7 into and along the holder 3 to complete loading.

Figure 8:
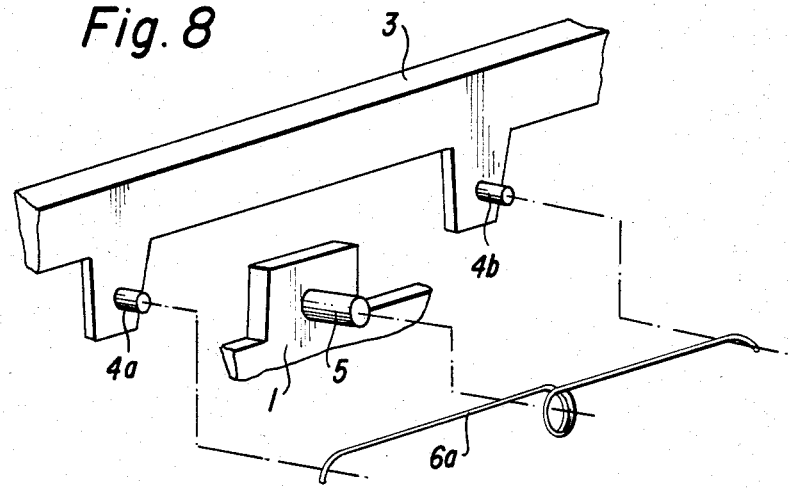
FIGS. 8 and 9 are oblique views of main parts showing respective embodiments of urging mechanisms having resilient members, usable in this invention.

It is more effective to employ resilient members (torsion springs), as shown in FIG. 8, in place of the resilient members 6a, 6b to pressingly urge the two holder guides 4a, 4b simultaneously by a single resilient member, so as to achieve smoother operation as well as reduction of the number of parts.

Figure 9:
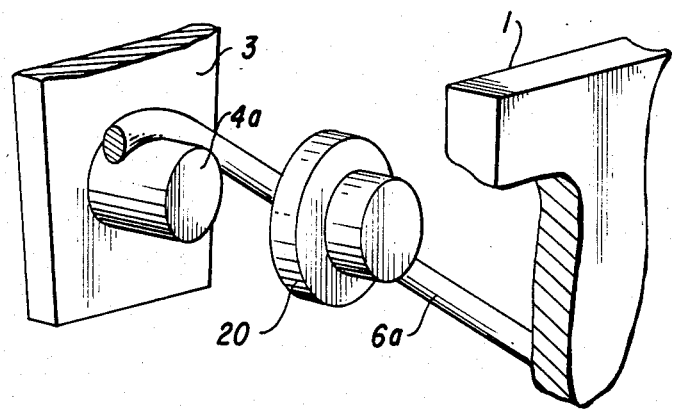

Also it is more effective to insert a flanged roller 20, as illustrated in FIG. 9, over the holder guides 4a to 4d because the smooth movement by the resilient members 6a, 6b in the gap between the sliding surfaces of the base body 1 and the holder 3 can be achieved, with limited lateral tolerance.

As is clear from the above descriptions, this invention realizes a compact recording medium loading apparatus with a reduced number of parts and reliable operation. Much effectiveness can be expected, particularly if the invention is applied e.g. to floppy disc drive apparatuses.

What is claimed is:

1. A loading apparatus for a recording medium comprising:
   a base body;
   means for holding a recording medium and holding means being reciprocally in vertical directions toward and away from the base body while keeping a horizontal orientation, said holding means being urged in a direction toward said base body;
   holder guide means, provided on said holding means, for guiding the movement of said holding means;
   at least one slide plate reciprocally movable in directions parallel with inserting and discharging directions of the recording medium and being urged in a direction parallel with the discharging direction of the recording medium;
   at least one raised member, provided on said at least one slide plate, for supporting said holder guide means against the urged direction of said holding means when the recording medium is not inserted into said holding means;
   said at least one raised member, when the recording medium is fully inserted into said holding means, being pushed by the recording medium to a position in which said raised member releases the holder guide means so that said holding means moves in the vertical direction toward said base body;
   a discharging plate reciprocally movable in directions parallel with the moving directions of said at least one slide plate and being urged in a direction parallel with the discharging direction of the recording medium; and at least one cam member, provided on said discharging plate, said at least cam member, when said discharging plate is moved by an external force in a direction against the urged direction of said discharging plate, pushing up said holder guide means in the direction away from said base body, thereby moving said holding means in a vertical direction away from said base body to a position where said holder guide means is supported by said at least one raised member.

2. The apparatus according to claim 1, wherein said holder guide means comprises a guide member inserted into an opening provided on a side wall of said base body.

3. The apparatus according to claim 2, wherein said at least one raised member is abutted at an upper side by said guide member and has an extended portion which is to abut on an end of the recording medium when the recording medium is not inserted into said holding means thereby being pushed in the inserting direction of the recording medium.

4. The apparatus according to claim 1, further comprising a clamp means, abutting on said holding means, for holding the recording medium upon loading the recording medium and for releasing the recording medium in response to the movement of said holding means upon discharging the recording medium.

5. A loading apparatus for a recording medium comprising:
a base body;
means for holding a recording medium and being reciprocally movable toward and away from the base body, and holding means being urged in a direction toward said base body;
holder guide members provided on a bottom wall of said holding means and inserted into slots provided on side walls of said base body so as to be reciprocally movable toward and away from said base body along said slots;
at least one slide plate reciprocally movable in directions parallel with said bottom wall of said holding means and being urged in a direction parallel with a discharging direction of the recording medium;
raised members fixed on said at least one slide plate for supporting said holder guide members against the urged direction of said holding means when the recording medium is not fully inserted into said holding means, one of said raised members being abuttable with an end of the recording medium when the recording medium is deeply into said holding means, thereby being pushed by the inserted recording medium, and said raised members, when the recording medium is fully inserted into said holding means, releasing said guide members to be movable toward said base body so that said holding means moves toward said base body;
a discharging plate reciprocally movable in a direction parallel with said bottom wall of said holding means and being urged in the discharing direction of the recording medium;
cam members fixed on said discharging plate, said cam members, when said discharging plate is moved by an external force in a direction against the urged direction of said discharging plate, pushing upward said holder guide members in the direction away from said base body, thereby moving said holding means away from said base body to a position where said raised members are moved in the urged direction of said at least one slide plate to a position for supporting said holder guide members.

6. The apparatus according to claim 5, further comprising: clamp means, abutting on said holding means, for holding the recording medium upon loading the recording medium and for releasing the recording medium in response to the movement of said holding means upon discharging the recording medium.

* * * * *